May 2, 1967 R. KORDES Plant Pat. 2,734
ROSE PLANT
Filed April 22, 1966
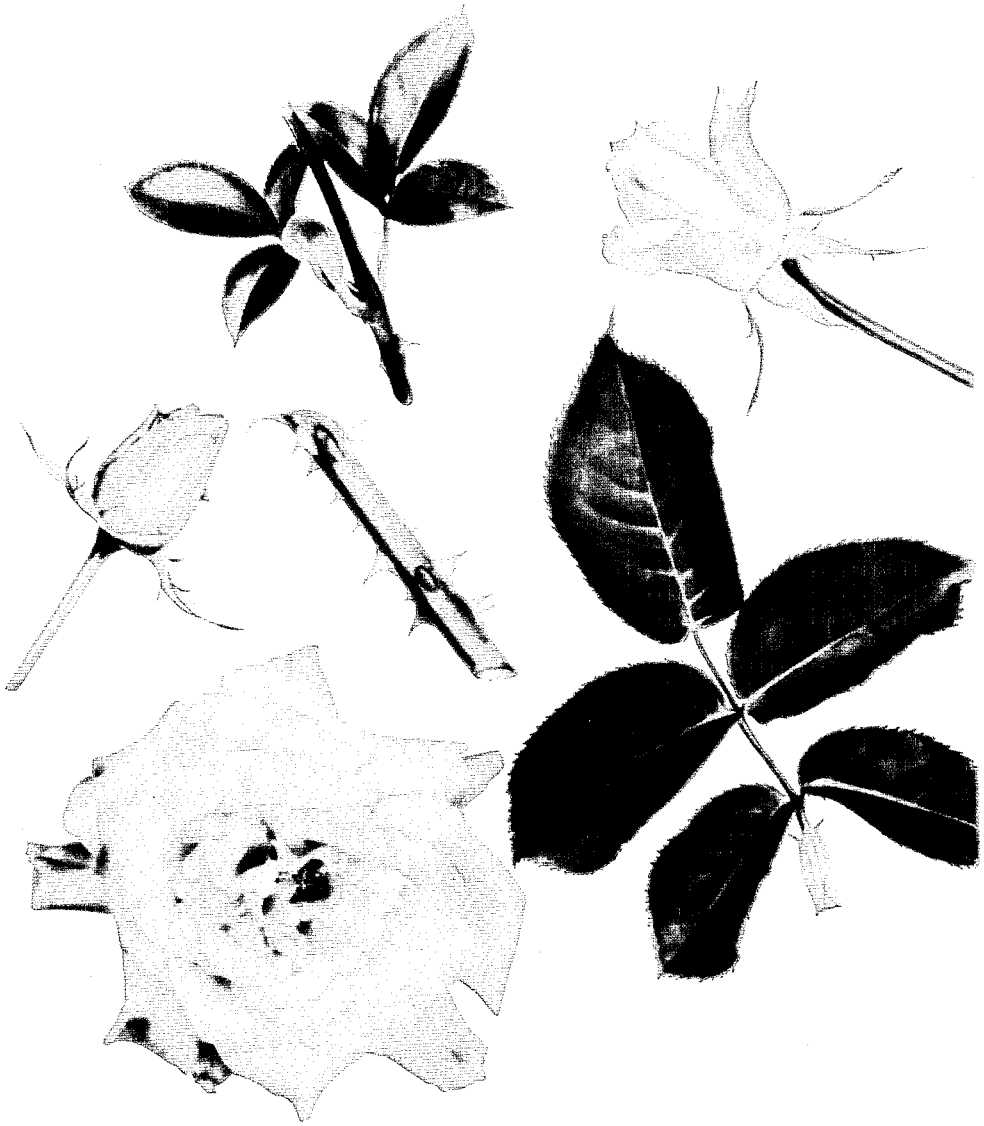
Inventor.
Reimer Kordes
By: Robbs & Robb
Attorneys.

United States Patent Office

Plant Pat. 2,734
Patented May 2, 1967

2,734
ROSE PLANT

Reimer Kordes, Barmstedt, near Elmshorn, Germany, assignor to Jackson & Perkins Company, Newark, N.Y., a corporation of New York

Filed Apr. 22, 1966, Ser. No. 544,633
1 Claim. (Cl. Plt.—20)

The present invention relates to a new and distinct variety of rose plant of the hybird tea class, which was originated by me by crossing the variety known as "Friedrich Schwarz" (unpatented) with the variety known as "Kordes Perfecta" (U.S. Plant Patent No. 1,604).

The primary objective of this breeding was to produce a new rose variety having a vigorous growing habit and which bears red flowers, while attaining sufficient growth and bloom to be well balanced. This objective was fully achieved, along with other desirable features, as evidenced by the following unique combination of characteristics which are outstanding in the new variety and which distinguish it from its parents, as well as from all other varieties of which I am aware:

(1) A vigorous, upright and well balanced plant habit, with the attainment of an average height of about 5½ feet.

(2) Free production of large flowers suitable for cut-flowers;

(3) An urn-shaped bud form;

(4) A high-centered open flower form;

(5) A distinctive and attractive Scarlet-Red general color tonality of the flowers; and (6) A strong and rich tea fragrance of the flowers.

Assexual reproduction of the new variety by budding, as performed at Newark, N.Y., U.S.A., and also at Pleasanton, Calif., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—"Friedrich Schwarz."
- *Pollen parent.*—"Kordes Perfecta."

Classification:
- *Botanic.*—Hybird tea.
- *Commercial.*—Hybird tea.

*Flower*

(Observations made from specimens grown outdoors at Newark, N.Y., U.S.A., in the early morning near the middle of the month of August.)

Blooming habit: Recurrent—continuous.

Bud:
- *Size.*—Large.
- *Form.*—Urn-shaped; is not affected by wet or hot weather.
- *Color.*—When sepals first divide—Oxblood Red, Plate 1. When petals begin to unfurl—Carmine, Plate 1. When half-blown—inside of petals—Spectrum Red, Plate 1; reverse of petals—Carmine, Plate 1, lightly overcast with Scarlet-Red, Plate 1.
- *Sepals.*—Branched; curl back when petals begin to unfurl. Color: inside—Deep Chrysolite Green, Plate 31; outside—Biscay Green, Plate 17.

- *Calyx.*—Color—Light Elm Green, Plate 17. Shape—funnel. Size—long. Aspect—smooth. Odor when rubbed—none.
- *Peduncle.* — Length — medium. Aspect — prickly. Strength—erect; heavy. Color—Buffy Citrine, Plate 16.
- *Opening.*—Opens up well; is not affected by adverse weather conditions.

Bloom:
- *Size.*—Large. Average size when fully expanded—6 inches.
- *Borne.*—Singly.
- *Stems.*—Long; strong.
- *Form (when first open).*—High-centered. Permanence—retains its form to the end.
- *Petalage.*—Double (full but open center). Number of petals under normal conditions—from 35 to 40.
- *Color.*—Center of flower—Scarlet-Red, Plate 1, very lightly overcast with Carmine, Plate 1. Outer petals—Scarlet-Red, Plate 1, very lightly over-cast with Spectrum Red, Plate 1. Base of petals (aiglet)—Lemon Chrome, Plate 4. Inside of petals—Scarlet-Red, Plate 1. Reverse of petals—Spectrum Red, Plate 1, very lightly overcast with Nopal Red, Plate 1. General tonality from a distance—Scarlet-Red, Plate 1.
- *Discoloration.*—General tonality at end of first day—Scarlet-Red, Plate 1, very lightly overcast with Carmine, Plate 1. Second day—Scarlet-Red, Plate 1. Third day—Scarlet-Red, Plate 1.

Petals:
- *Texture.*—Leathery; is not affected by wet or hot weather.
- *Apperance.*—Inside—satiny. Outside—shiny.
- *Form.*—Oval.
- *Arrangement.*—Imbricated (regularly arranged shingel-like).
- *Petaloids in center.*—Few; large.
- *Persistence.*—Drop off cleanly.
- *Fragrance.*—Strong. Nature—tea (average hybird tea scent).
- *Lasting quality.*—On the plant—long. As cut flower—long.

*Genital organs*

Stamens, anthers: Medium size; many; regularly arranged around styles. Color—Ochraceous-Orange, Plate 15.

Stamens, filaments (threads): Medium length. Color—Light Jasper Red, Plate 13.

Pollen: Color—Light Ochraceous-Buff, Plate 15.

Styles: Loosely separated; uneven length; medium length; thin.

Stigmas: Color—Warm Buff, Plate 15.

Ovaries: All enclosed in calyx.

Hips: None.

Seeds: None.

*Plant*

Form: Bush.

Growth: Vigorous; upright; attains an average height of about 5½ feet.

Foliage: Compound of 3–5 leaflets.
- *Size.*—Large.
- *Quantity.*—Normal.
- *Color.*—New foliage: upper side—Spinach Green, Plate 5; under side—Light Cress Green, Plate 31. Old foliage: upper side—Cress Green, Plate 31; under side—Kronberg's Green, Plate 31.
- *Shape.*—Oval pointed.
- *Texture.*—Upper side—leathery. Under side—smooth.
- *Ribs and veins.*—Ordinary.
- *Edge.*—Serrated (saw toother).

*Serration.*—Both double and single; large.

*Leaf stem.*—Color—Buffy Citrine, Plate 16. Under side—prickly.

*Stipules.*—Long; bearded.

Wood:

*New wood.*—Color—Madder Brown, Plate 13. Bark—smooth.

*Old wood.*—Color—Chromium Green, Plate 32. Bark—smooth.

Thorns:

*Thorns.*—Quantity: on main stalks from base—many; on laterals from stalk—many. Form—narrow base; medium length; some hooked downward and some hooked upward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novely by the unique combination of a vigorous, upright and well balanced plant habit, with the attainment of an average height of about 5½ feet, free production of large flowers suitable for cut flowers, an urn-shaped bud form, a high-centered open flower form, a distinctive and attractive Scarlet-Red general color tonality of the flowers, and a strong and rich tea fragrance of the flowers.

No references cited.

ANTONIO F. GUIDA, *Acting Primary Examiner.*

ROBERT E. BAGWILL, ABRAHAM G. STONE, *Examiners.*